United States Patent
Dierre et al.

(10) Patent No.: US 9,646,731 B2
(45) Date of Patent: May 9, 2017

(54) X-RAY RADIATION DETECTOR, CT SYSTEM AND RELATED METHOD

(71) Applicant: Siemens Aktiengesellschaft, Munich (DE)

(72) Inventors: Fabrice Dierre, Granville (FR); Edgar Göderer, Forchheim (DE); Peter Hackenschmied, Nuremberg (DE); Steffen Kappler, Effeltrich (DE); Björn Kreisler, Hausen (DE); Miguel Labayen De Inza, Forchheim (DE); Daniel Niederlöhner, Erlangen (DE); Mario Reinwand, Breitbrunn (DE); Christian Schröter, Bamberg (DE); Karl Stierstorfer, Erlangen (DE); Matthias Strassburg, Klagenfurt (AT); Justus Tonn, Forchheim (DE); Stefan Wirth, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 108 days.

(21) Appl. No.: 14/418,093

(22) PCT Filed: Jul. 9, 2013

(86) PCT No.: PCT/EP2013/064492
§ 371 (c)(1),
(2) Date: Jan. 29, 2015

(87) PCT Pub. No.: WO2014/019817
PCT Pub. Date: Feb. 6, 2014

(65) Prior Publication Data
US 2015/0221406 A1   Aug. 6, 2015

(30) Foreign Application Priority Data
Jul. 31, 2012  (DE) .......................... 10 2012 213 409

(51) Int. Cl.
*G01T 1/24* (2006.01)
*G21K 1/02* (2006.01)
(Continued)

(52) U.S. Cl.
CPC ............. *G21K 1/02* (2013.01); *G01N 23/046* (2013.01); *G01T 1/24* (2013.01); *G01T 1/241* (2013.01); *G01T 1/2985* (2013.01)

(58) Field of Classification Search
CPC combination set(s) only.
See application file for complete search history.

(56) References Cited

U.S. PATENT DOCUMENTS 7,652,258 B2   1/2010  Shahar et al.
2004/0079891 A1   4/2004  Sato et al.
(Continued)

FOREIGN PATENT DOCUMENTS

CN   1484321 A   3/2004
CN   1912651 A   2/2007
(Continued)

OTHER PUBLICATIONS

English translation of German Office Action issued in German Patent Application No. 10 2013 214 684, dated Oct. 28, 2015.
(Continued)

*Primary Examiner* — Phillip A Johnston
*Assistant Examiner* — Hsien Tsai
(74) *Attorney, Agent, or Firm* — Harness, Dickey & Pierce PLC (57) ABSTRACT

A direct-converting x-ray radiation detector is disclosed for detecting x-ray radiation, in particular for use in a CT system. In an embodiment, the detector includes a semiconductor material used for detecting the x-ray radiation; at least one collimator; and at least one radiation source, to irradiate the semiconductor material with additional radia-
(Continued)

tion. In at least one embodiment, the at least one collimator includes at least one reflection layer on a side facing the semiconductor material, on which the additional radiation is reflected to the semiconductor material. In another embodiment, a CT system including the direct-converting x-ray radiation detector, and a method for detecting incident x-ray radiation via a direct-converting x-ray radiation detector, in particular for use in a CT system, are disclosed.

25 Claims, 3 Drawing Sheets (51) Int. Cl.
    *G01T 1/29*           (2006.01)
    *G01N 23/04*       (2006.01)

(56) References Cited

U.S. PATENT DOCUMENTS

| | | |
|---|---|---|
| 2006/0038188 A1 | 2/2006 | Erchak et al. |
| 2007/0034807 A1 | 2/2007 | Danzer et al. |
| 2007/0131867 A1* | 6/2007 | Okada .................. G01T 1/2018 250/370.09 |
| 2008/0137004 A1 | 6/2008 | Iwasaki et al. |
| 2008/0164418 A1* | 7/2008 | Shahar .................. G01T 1/24 250/370.01 |
| 2010/0086098 A1 | 4/2010 | Shahar et al. |
| 2011/0253886 A1 | 10/2011 | Hackenschmied et al. |
| 2015/0221406 A1 | 8/2015 | Dierre et al. |

FOREIGN PATENT DOCUMENTS

| | | |
|---|---|---|
| DE | 2255465 A1 | 5/1973 |
| DE | 102010015422 A1 | 10/2011 |
| DE | 102012200549 B3 | 4/2013 |
| DE | 102012213409 B3 | 11/2014 |
| WO | WO-2013/120657 A1 | 8/2013 |
| WO | WO-2014/019817 | 2/2014 |

OTHER PUBLICATIONS

German Examination Report mailed Jun. 25, 2013 for corresponding German Application No. 102012213409.3.
International Search Report PCT/ISA/210 for International Application No. PCT/EP2013/064492 dated Dec. 2, 2013.
Written Opinion of the International Searching Authority PCT/ISA/237 for International Application No. PCT/EP2013/064492 dated Dec. 2, 2013.
U.S. Office Action issued in U.S. Appl. No. 14/327,630, dated Nov. 18, 2015.
Scheubeck M: "Thermische Anforderungen von LED-Leuchten", www.all-electronics.de [online] (Jun. 18, 2012).
German Office Action issued in German Patent Application No. 10 2013 214 684, dated Oct. 28, 2015.
Office Action dated May 23, 2016 in Chinese Application No. 201380048285X.
Chinese Office Action issued Feb. 3, 2017 in Chinese Application No. 201380048285X.

\* cited by examiner

X-RAY RADIATION DETECTOR, CT SYSTEM AND RELATED METHOD

PRIORITY STATEMENT

This application is the national phase under 35 U.S.C. §371 of PCT International Application No. PCT/EP2013/064492 which has an International filing date of Jul. 9, 2013, which designated the United States of America, and which claims priority to German patent application DE 102012213409.3 filed Jul. 31, 2012, the entire contents of each of which are hereby incorporated herein by reference.

FIELD

At least one embodiment of the invention generally relates to a direct-converting X-ray radiation detector for detecting X-ray radiation, at least including a semiconductor material used for detecting the X-ray radiation, at least one collimator, and at least one radiation source, which irradiates the semiconductor material with additional radiation, and a CT system with an X-ray radiation detector. At least one embodiment of the further generally relates to a method for detecting incident X-ray radiation via a direct-converting X-ray radiation detector.

BACKGROUND

For the detection of gamma and X-ray radiation, in particular in CT, dual-energy CT, SPECT and PET systems, use is made inter alia of direct-converting detectors, based on semiconducting materials, such as CdTe, CdZnTe, CdZnTeSe, CdTeSe, CdMnTe, InP, TlBr2, HgI2. However, with these materials the effect of polarization arises, in particular with a high radiant flux density necessary for CT devices.

Polarization means the reduction in the detected count rate at high photon or radiant fluxes. This polarization is caused by the very low mobility of the charge carriers, especially the electron voids or holes, and by the concentration of intrinsic impurities in the semiconductor. The polarization thus arises due to the reduction in the electric field because of localized charges linked to impurities, the charges acting as capture and recombination centers for the charge carriers generated by the X-ray radiation. The result is a reduction in the service life and mobility of charge carriers, which in turn leads to a reduction in the detected count rate at the high radiant flux density.

The polarization of the semiconductor material changes during a measuring process. This change in the electric field in turn results in a change in the measured pulse heights and thus also affects the count rate of the semiconductor detector, also referred to as drift. Thus due to the polarization the maximum detectable radiant flux of a direct converter is limited. In particular in the case of a high radiant flux density necessary for CT devices the effect of the polarization is amplified. For this reason it has not until now been possible to convert high radiation densities, as used especially in computed tomography, directly into electrical pulses. The detector signal can no longer be directly linked to the attenuation of the object to be measured.

This problem has not as yet been completely solved. One possible solution is to largely forestall the polarization of the semiconductor material by irradiating the detector with additional X-ray radiation, this additional irradiation being performed immediately before a measuring process. However, this method is not suitable for patient operation, since the patient would be exposed to an additional dose. Due to the additional X-ray irradiation before the measuring process a pre-biased state of the detector is set, and the semiconductor material is thus deliberately polarized, so that both calibration measurements and actual measuring processes can be performed.

Another possible solution is to perform measuring processes with a constant current feed value of the detector. This means the quasi-Fermi levels can be kept constant. This is done for example by generating additional charge carriers in the semiconductor material before the incidence of the X-ray radiation to be detected. If the actual X-ray irradiation starts, the impurities are already populated with charge carriers, corresponding to the state of equilibrium under X-ray irradiation. The polarization of the semiconductor material is equalized. The electrical field thus stays constant during the measuring process and a unique link can be created between an attenuation by the examined object and the count rate of the detector.

In another possible solution the semiconductor material is irradiated with infrared radiation. This irradiation results in a conditioning of the detector which is similar to irradiation with X-ray radiation, the IR radiation being easy to manage and harmless for the patient. In the past, it has been known to irradiate the semiconductor material through the planar cathode. However, direct irradiation of the semiconductor material is difficult, since the direct radiation path onto the semiconductor material is restricted by the scattered radiation grid. For uniform irradiation there consequently remains only a narrow gap between the bottom of the scattered radiation grid and the top of the semiconductor. No solution to this problem is known to date.

SUMMARY

At least one embodiment of the invention is directed to creating a direct-converting X-ray radiation detector, in which a uniform irradiation of the semiconductor materials used for detection is possible and so the polarization of the semiconductor material or the drift of the detector is prevented. Further, at least one embodiment is directed to a method for operating such an X-ray radiation detector.

Advantageous developments of the invention form the subject matter of subordinate claims.

The inventors have recognized that uniform irradiation of the semiconductor material can be achieved in an X-ray radiation detector by the latter being irradiated indirectly. For this purpose a coating is applied in a gap between the collimator and the semiconductor material on the side of the collimator opposing the semiconductor material, which coating reflects the additional radiation uniformly onto the semiconductor. The semiconductor material is consequently irradiated indirectly. The advantage of this is that the radiation can be irradiated onto the semiconductor not merely through a small gap between semiconductor material and collimator, but because of the reflection off the coating the irradiation is uniform and covers a wide area. Accordingly this reflection layer can consequently be irradiated from a light source arranged outside the gap between semiconductor material and collimator, with the reflection layer reflecting the radiation onto the semiconductor material.

The radiation penetrates an at least partially transparent electrode attached to the semiconductor material and in the semiconductor material generates additional charge carriers near to the surface. A multiple reflection between the electrode on the semiconductor material and the reflection layer is also possible here. Due to the reflection of the additional radiation the semiconductor is uniformly irradiated across its entire surface. Accordingly charge carriers are generated uniformly, with the additional charge carriers populating the impurities of the semiconductor crystal, i.e. forming stationary charges which counter the X-ray-radiation-conditioned polarization of the semiconductor. The polarization is consequently prevented.

Light-emitting diodes are for example suitable as light sources, i.e. as a radiation source for the additional radiation. The energy of the radiation lies for example in the infrared range (IR radiation for short). The reflection layer and the collimator are designed such that as uniform an irradiation as possible and thus a uniform generation of charge carriers is supported on the entire surface of the semiconductor material. Firstly the reflection layer has as high a reflectance as possible for this purpose and secondly the reflection layer is as transparent as possible for the X-ray radiation to be detected. Examples of suitable reflecting materials include reflector paints which have a high reflectivity and sensitivity in respect of the X-ray irradiation. Also suitable are materials such as metals, in particular light metals, in the form of metallic films or metalized surfaces, plastics, in particular laminated plastics, compounds such as metal alloys or semiconductors. The collimator can be coated with the reflection layer using standard deposition methods such as vaporization, sputtering, chemical or physical deposition.

Different embodiments of the reflection layer are possible, wherein regardless of the respective form of embodiment a uniform, indirect irradiation of the semiconductor material is achieved by means of the reflection, including multiple reflection, of the IR radiation, which is laterally incident into the gap, between semiconductor material and collimator. Accordingly the reflection layer can for example be flat on the collimator, i.e. with a uniform thickness, curved and/or structured. Furthermore, the reflection layer extends, for the uniform irradiation of the semiconductor, across the entire side of the collimator.

A curved reflection layer has a concave curvature. This means that one side of the reflection layer is designed to be raised or thickened or intensified compared to another side of the reflection layer in the direction of the semiconductor material. Here either the side of the collimator facing the semiconductor is curved, on which then a uniformly thick reflection layer is applied, and/or the reflection layer itself is curved, wherein the collimator is designed to be flat or at least less curved. The height of the curvature is here limited by the width of the gap, in other words the distance between collimator and semiconductor.

The curvature of the reflection layer and/or of the collimator is designed such that as uniform as possible an irradiation of the semiconductor is achieved. To this end the curvature can especially be aligned to the radiation pattern of the light source, and to the distance between the light source and the reflection layer and the semiconductor material, i.e. the whole light path, and in the case of multiple reflection to the radiation loss each time radiation is reflected off the collimator.

When the reflection layer is irradiated from several sides the shape of the curvature can have an appropriate symmetry. If for example the semiconductor material is illuminated from two opposing sides, the reflection layer can be designed such that the curvature consists of two sides which are as mirror-symmetrical as possible, the radii of which are each constructed on a single light source. If the reflection layer is irradiated for example by four light sources close to the corners of a rectangular semiconductor surface, the curvature of the reflection layer can consist of four symmetrically curved quadrants. Furthermore, the curvature of the reflection layer can also be aligned to several different light sources and the radiation patterns thereof.

In the case of a flat reflection layer it can be structurally designed to support a uniform irradiation of the semiconductor material with the reflected radiation. To this end the reflection layer has different reflection properties, the reflectivity of the reflection layer being reduced toward the radiation source. This can be achieved for example either by the reflection layer having openings or by an additional non-reflecting masking being applied to the reflection layer in part or by the material of the reflection layer having a different intrinsic reflectance, for example due to a different chemical composition. In this case the density or expansion of the modified positions can, if the radiation source radiates onto the reflection layer from a z direction, become smaller in this z direction, i.e. toward large z values. As the distance from the light source increases the reflectivity of the reflection layer becomes greater and vice versa. The reflection of the radiation is consequently reduced at small z values, at which it is more pronounced, so that the indirect irradiation of the semiconductor material becomes more homogenous. In an X-ray radiation detector of a CT system the z direction corresponds to the system axis of the CT system.

In another embodiment with a flat reflection layer, the permeability of the electrode arranged on the semiconductor material, opposing the reflection layer, can be reduced close to the radiation source. To this end the electrode can be designed to be partially interrupted, i.e. to have openings. An interruption or opening in the electrode means, in the case of an only partially transparent electrode, a higher transmission of the radiation into the semiconductor material and thus less reflection back to the reflection layer. The density or expansion of the openings can become larger at large z values, in other words away from the radiation source. This means that at large z values a higher proportion of the radiation is transmitted; at small z values more light is reflected and is thus available for higher z values due to multiple reflection. As the distance from the light source increases the transmission level of the electrode thus increases and vice versa.

In these embodiments of the reflection layer for the indirect irradiation of the semiconductor material, a gradient of the irradiation that occurs in the propagation direction of the additional radiation or in the z direction is equalized because of the radiation pattern of the radiation sources, the radiation path and the partial reflection. This means no uniform conditioning of the detector by a uniform generation of additional charge carriers can take place. A non-uniform detector response and image artifacts resulting therefrom are prevented. Furthermore, the rigidity of the reflection layer increases on the collimator due to the curvature as against the acceleration forces occurring during the rotation in a CT system.

Furthermore, in the case of indirect irradiation of the semiconductor material no active components which could suffer radiation damage or impair the dose efficiency of the system as a whole are arranged in the direct beam path of the X-ray radiation. The patient is also prevented from receiving an additional dose. Furthermore, the components used here, such as X-ray-resistant reflection materials and light-emitting diodes, are already well-established and thus are readily and cheaply available.

By irradiating the semiconductor material it is possible to prevent the drift of the detector response due to the polarization occurring in the semiconductor. Furthermore, due to the uniform irradiation before and/or during a measuring process other drift-sensitive components can also be conditioned. This relates in particular to components that without bias lighting would heat up during a measuring process.

Accordingly, the inventors propose improving a direct-converting X-ray radiation detector for detecting X-ray radiation, in particular for use in a CT system, at least having a semiconductor material used for detecting the X-ray radiation, at least one collimator, and at least one radiation source, which irradiates the semiconductor material with additional radiation, such that the at least one collimator has at least one reflection layer on a side facing the semiconductor material, off which the additional radiation is reflected onto the semiconductor material. In a direct-converting semiconductor detector of this type the semiconductor material is irradiated indirectly, the irradiation taking place uniformly distributed across its surface. Charge carriers are generated thanks to this additional irradiation, by means of which the polarization of the semiconductor material is prevented, so that the respective attenuation of the X-ray radiation can be assigned unambiguously to a count rate of the detector. A detector of this type is advantageously suitable for detecting the high radiant flux densities occurring in CT systems.

The detector comprises a semiconductor material which is used for detecting the X-ray radiation. Examples of suitable semiconductor materials include CdTe, CdZnTe, CdZnTeSe, CdTeSe, CdMnTe, InP, TlBr2 or HgI2. Furthermore the detector comprises at least one collimator for shielding against scattered radiation, which is arranged in the beam path of the X-ray radiation in front of the semiconductor material. Preferably the collimator is arranged on the same side of an examination object as the semiconductor material. An interspace in the form of a gap is designed between the collimator and the semiconductor material. An electrode is arranged in the gap on the semiconductor material in one embodiment. The electrode is preferably designed to be at least partially transparent.

Furthermore, the detector also comprises at least one radiation source for irradiation of the semiconductor material with additional radiation. In one embodiment precisely one radiation source is designed, though other embodiments provide for more than one radiation source, for example two, three or four radiation sources. For example, the radiation source is designed as a light-emitting diode, which preferably generates IR radiation with a wavelength of at least 780 nm. In another embodiment radiation with a wavelength in the visible range is used. The radiation source is preferably arranged to the side of the semiconductor material. More preferably the radiation source is arranged outside the gap between the collimator and the semiconductor material. Irradiation of the radiation source here advantageously takes place in the direction of the gap, so that the radiation is irradiated into the gap. In one embodiment the radiation source is arranged in a positive z direction in front of the semiconductor material; in another embodiment the radiation source is arranged in a positive z direction behind the semiconductor material. Accordingly the radiation source preferably radiates in and/or against the positive z direction. The collimator has a bottom facing one side of the semiconductor material. The side of the semiconductor opposing the bottom is designated as the top in what follows. The gap between semiconductor material and collimator is thus formed by the top of the semiconductor material and the bottom of the collimator.

According to an embodiment of the invention, the collimator has at least one reflection layer on its bottom, i.e. on the side facing the semiconductor material. The at least one reflection layer reflects the radiation, which is irradiated by the radiation source into the gap, onto the electrode or the top of the semiconductor material. Thus the semiconductor material is irradiated indirectly. The radiation can be partially reflected back off the electrode, so that a multiple reflection is possible in the gap. Advantageously a uniform irradiation and thus a uniform charge carrier generation is achieved on the entire side of the semiconductor material thanks to the radiation being reflected off the at least one reflection layer.

In one embodiment, precisely one reflection layer is designed. Other embodiments provide for more than one reflection layer, for example two, three or four reflection layers. Advantageously the reflection layer covers at least 50%, preferably at least 75% and more preferably at least 90%, of the bottom of the collimator. Most preferably the reflection layer covers the entire bottom of the collimator. Several reflection layers are for example formed next to one another and/or above one another. The reflection layers can be designed to be identical or different. To ensure as much of the radiation as possible is reflected, the reflectance of the reflection layer or of the material of the reflection layer is as high as possible. In one embodiment the reflectance is at least 50%, preferably at least 90% and most preferably at least 99%, of the incident radiation.

Furthermore, the reflection layer can be shaped or structured differently. In one embodiment the reflection layer is designed to be parallel to the top of the semiconductor. Accordingly the reflection layer is preferably designed to be flat. Accordingly the reflection layer advantageously has a uniform thickness. The thickness of the reflection layer is preferably between 1 μm and 1 mm. The advantageously used IR radiation advantageously barely penetrates the material of the reflection layer, so that the thickness of the reflection layer represents a negligible parameter. Here the surface of the reflection layer preferably runs parallel to the bottom of the collimator.

In another embodiment, the reflection layer is designed to be non-parallel to the top of the semiconductor. Preferably the reflection layer is designed to be curved, i.e. it has at least one curvature. In this case the reflection layer is concavely curved toward the semiconductor material, for example with a depression and at least one raised side. The curvature arises either as a result of a uniformly thick reflection layer on a curved bottom of the collimator or of a reflection layer of varying thickness, which is thus correspondingly curved.

One embodiment of the reflection layer provides for precisely one curvature. The one curvature is preferably raised in the z direction. This means the reflection layer is higher or thicker with large z values than with small z values. In one embodiment the curvature is curved or raised as the distance from the radiation source increases. Another embodiment provides for several curvatures of the reflection layer. Several curvatures are preferably designed to be symmetrical. Furthermore, several curvatures can have the same radius or different radii. For example, two curvatures are arranged opposing one another, so that the one reflection layer is designed to be semicircular in shape. Preferably the raised regions of the reflection layer are respectively arranged at small z values, i.e. close to the radiation source, or at large z values, i.e. remote from the radiation source.

In a further embodiment, the reflection layer has four curvatures. This embodiment is suitable for example for a rectangular embodiment of the semiconductor material with several, preferably four, radiation sources each arranged at the corners of the semiconductor material. The four curvatures are advantageously designed as symmetrical quadrants, which form a reflection layer that is hemispherical in shape overall.

By means of a curved reflection layer, a uniform irradiation of the semiconductor material is ensured thanks to a selective deflection of the reflected radiation. In this case the shape of the reflection layer or the number of curvatures is advantageously adjusted to the number and direction of incidence of the radiation sources. With two opposing curvatures two opposing light sources advantageously each radiate onto the opposing curvature of the reflection surface. Furthermore the shape of the curvatures is advantageously adjusted to a radiation pattern of the radiation source, to a distance between the radiation source and the reflection layer and the semiconductor material, and in the case of a multiple reflection to the radiation losses that occur. A height of the curvature is here limited by the width of the gap.

The reflection layer can be designed to be variable or identical in the propagation direction of the additional radiation, in particular in the z direction. Advantageously the reflection layer is designed along the z direction such that during an irradiation of the semiconductor material as uniform an irradiation and charge carrier generation as possible is ensured in the z direction across the entire z direction.

In one embodiment the material properties of the reflection layer vary as the distance from the radiation source varies. In other words, with a radiation source radiating in the z direction, the reflection layer is designed with material properties that vary, i.e. differ, in the z direction or in the propagation direction of the additional radiation. These material properties are for example the thickness, the density, the reflectance and/or a material composition. For example, the reflectance varies in the z direction. Advantageously the reflectance increases in the z direction, so that at small z values, i.e. close to the radiation source, a smaller reflection occurs. This can be achieved by varying the density, by a different intrinsic reflectance, by openings in the reflection layer and/or by an additional non-reflecting masking of the reflection layer. If the reflectance is varied by means of openings in the reflection layer, a size of the openings advantageously decreases in the z direction.

In another embodiment to this end, the permeability of an electrode attached to the semiconductor material in the gap can be designed to be different in the z direction or the propagation direction of the additional radiation. The electrode is preferably arranged on the top of the semiconductor material, which opposes the bottom of the collimator with the reflection layer. For example, the electrode has at least one opening. Accordingly the permeability for the additional radiation, i.e. the transmittance, of the electrode in openings is increased. Advantageously a number and/or a size of the openings becomes larger in the z direction, so that an opening remote from the radiation source is larger than an opening close to the radiation source.

Another embodiment provides for a multilayer reflection layer. Advantageously the individual layers have different levels of reflectance, with an outermost layer preferably having a smaller reflectance than an inner layer. Outer layers can for example have openings, so that by means of these openings the reflection layer has a different reflection behavior overall. For example, by means of an outermost, structured layer with a very low reflectance a virtually non-reflecting masking is embodied on the reflection layer.

Suitable materials for the reflection layer are those which firstly are as transparent as possible for the radiation to be detected and secondly reflect the radiation from the radiation source as well as possible. Examples include reflector paint, metals, in particular light metal such as aluminum or magnesium, plastics, for example polyethylene, in particular polyethylene with a vacuum-metalized aluminum coating, and compounds, in particular metal alloys and/or semiconductors. Such materials can easily be applied to the bottom of the collimator by means of known deposition methods such as vaporization, sputtering, chemical or physical deposition.

The scope of at least one embodiment of the invention also includes a CT system, comprising an X-ray radiation detector, with which tomographic recordings of an examination object can be generated. In the case of a CT system with an inventive direct-converting X-ray radiation detector a drift-free measurement of the radiation absorption is advantageously ensured, so that the recordings generated are advantageously free of image artifacts. The system axis of the CT system here corresponds to the z direction, wherein the z direction is oriented perpendicular to a direction of incidence of the X-ray radiation to be detected.

The scope of at least one embodiment of the invention further relates to a method for detecting incident X-ray radiation by means of a direct-converting X-ray radiation detector, in particular for use in a CT system, with a semiconductor material used for detection being indirectly irradiated for the generation of additional charge carriers with additional radiation by means of at least one reflection layer. The irradiation of the semiconductor material takes place preferably by one or more additional radiation sources, which irradiate a reflection layer designed opposite the semiconductor material on a collimator, with the reflection layer reflecting the additional radiation onto the semiconductor material. Furthermore, the radiation is reflected off the reflection layer and/or an electrode on the semiconductor material either once and/or multiple times. By irradiating the semiconductor material, additional charge carriers are advantageously generated, which counter the polarization occurring in the semiconductor material during the detection of the X-ray radiation. The additional radiation is preferably IR radiation.

In a preferred embodiment, the irradiation of the reflection layer takes place along the z direction. Here a number of additionally generated charge carriers decreases in or against the z direction. To prevent this and to generate many charge carriers uniformly along the z direction, in one embodiment the reflectance of the at least one reflection layer increases in the z direction. Consequently a reflection layer with a different reflectance in the propagation direction of the additional radiation and/or in the z direction of an X-ray radiation detector built into a CT system is advantageously used.

In another embodiment, the transmittance of an electrode attached to the semiconductor material, opposing the at least one reflection layer, increases in the z direction. Thus an electrode with a transmittance which is different in the propagation direction of the additional radiation and/or in the z direction of an X-ray radiation detector built into a CT system is advantageously used. Thanks to the increased reflection in the z direction and/or thanks to the greater permeability in the z direction or the higher transmittance of the electrode, charge carriers are increasingly generated remotely from the radiation source, so that overall the charge carriers are uniformly generated in the z direction.

Furthermore, the additional indirect irradiation of the semiconductor material preferably takes place before and/or during the incidence of the X-ray radiation to be detected. Advantageously the additional irradiation starts at least 5 s, preferably at least 10 s and more preferably at least 15 s before the start of a measuring process with the X-ray radiation.

BRIEF DESCRIPTION OF THE DRAWINGS

The invention is described in greater detail below on the basis of the preferred example embodiments with the help of the figures, wherein only the features necessary for the understanding of the invention are depicted. The following reference characters are used: 1: semiconductor; 2: collimator; 3: reflection layer; 4: electrode; 5: gap; 6: light-emitting diode; 7: path of the reflectance; 8: path of the transmittance; C1: CT system; C2: first X-ray tube; C3: first detector; C4: second X-ray tube (optional); C5: second detector (optional); C6: gantry housing; C7: patient; C8: patient couch; C9: system axis; C10: arithmetic and control unit; d: drift; Prg1 to Prgn: computer programs; t: time.

In detail.

DETAILED DESCRIPTION OF THE EXAMPLE EMBODIMENTS

Figure 1:
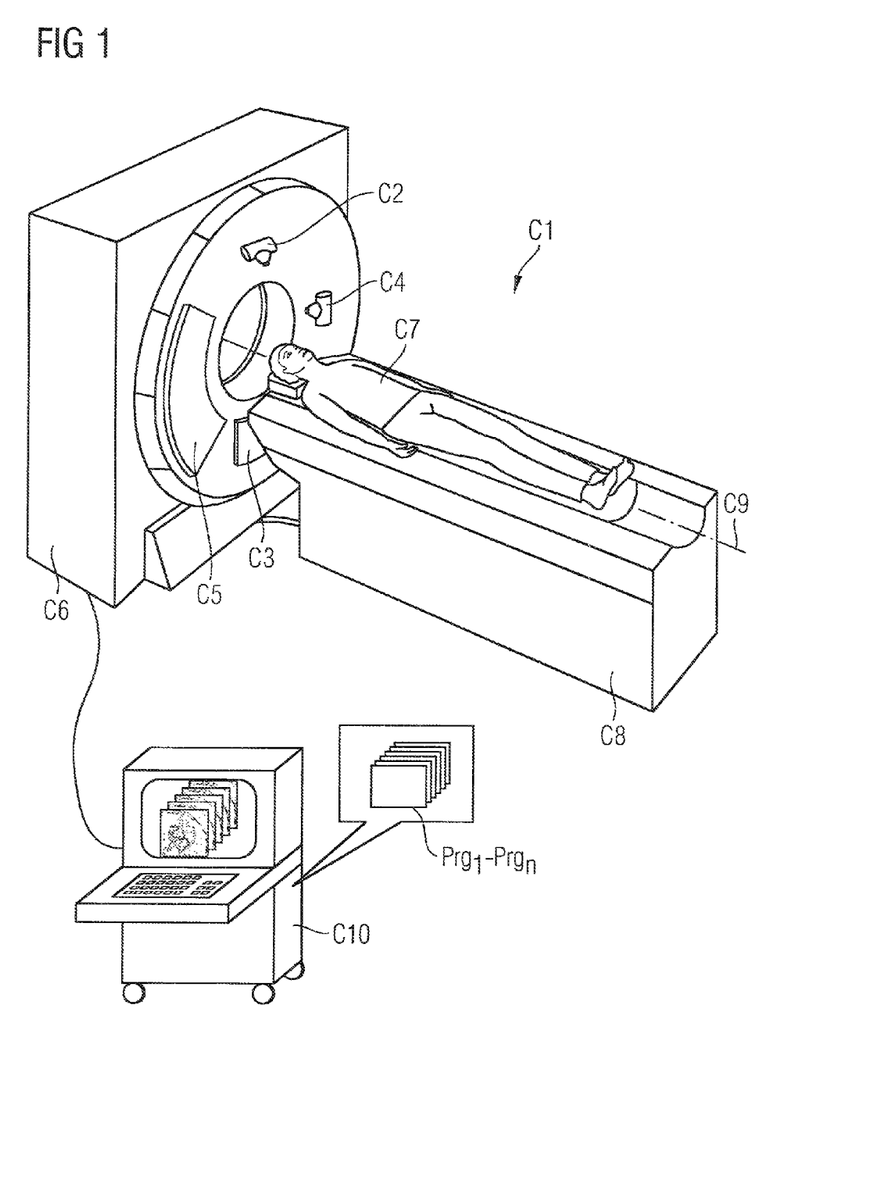
FIG. 1 shows a schematic depiction of a CT system with arithmetic unit.

FIG. 1 shows an exemplified CT system C1. The CT system C1 comprises a gantry housing C6, in which is located a gantry (not depicted in greater detail here), to which a first X-ray tube C2 with an opposing first detector C3 is attached. Optionally a second X-ray tube C4 with a second opposing detector C5 is provided. A patient C7 is located on a patient couch C8 which can be displaced in the direction of the system axis C9, and with which during the scanning with the X-ray radiation he can be continuously or sequentially pushed along the system axis C9 or in the z direction through a measuring field between the X-ray tubes C2 and C4 and the respectively assigned detectors C3 and C5. This procedure is controlled by an arithmetic and control unit C10 with the help of computer programs Prg1 to Prgn.

Figure 2:
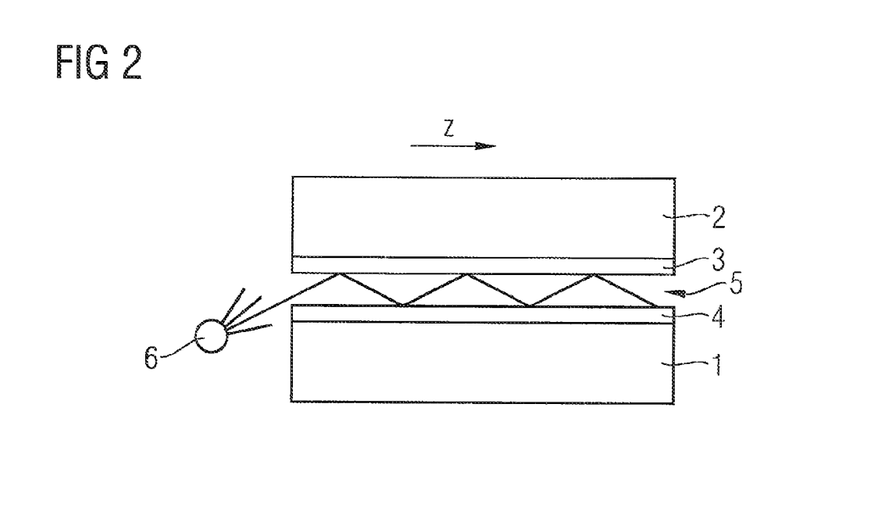
FIG. 2 shows a schematic, partial depiction of an X-ray radiation detector in a first embodiment.
Figure 4:
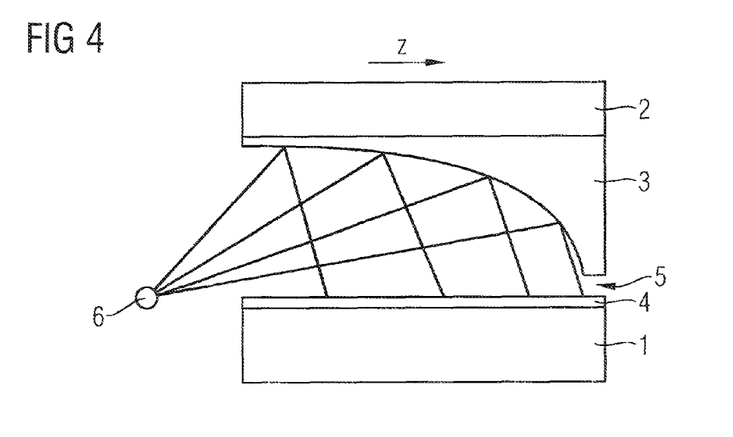
FIG. 4 shows a schematic, partial depiction of the X-ray radiation detector in a further embodiment.
Figure 5:
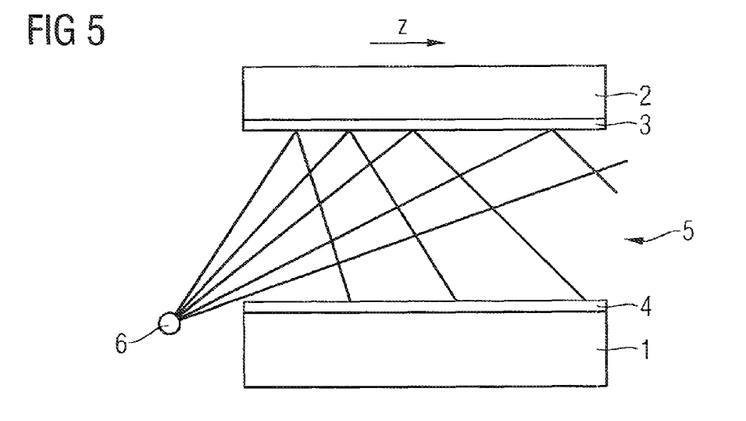
FIG. 5 shows a schematic, partial depiction of the X-ray radiation detector in a further embodiment

In the exemplified embodiment of the CT system C1 shown here the detectors C3 and C5 are embodied as direct-converting X-ray radiation detectors which have at least one semiconductor material used for detecting the X-ray radiation, a collimator, and a laterally arranged radiation source which irradiates the semiconductor material with additional radiation (see FIGS. 2, 4 and 5). The CT system C1 is accordingly operated in accordance with an embodiment of the inventive method.

FIGS. 2, 4 and 5 each schematically depict a semiconductor material 1 of a detector element used for detecting X-ray radiation in a CT system (see FIG. 1). The semiconductor material 1 is for example CdTe. Furthermore, a collimator 2 is depicted, which is arranged at a distance from and parallel to the semiconductor material 1. A gap 5 is designed between the semiconductor 1 and the collimator 2. The semiconductor 1 has an electrode 4 on its side opposing the collimator 2, said electrode 4 having a particular transmittance. The electrode 4 is connected to electronics of the CT system, which however are not depicted for the sake of clarity. On a front side, viewed in the z direction, of the semiconductor 1 a radiation source is arranged outside the gap 5 in the form of a light-emitting diode 6. The light-emitting diode 6 radiates in the z direction into the gap 5. The radiation is infrared radiation.

According to an embodiment of the invention, a reflection layer 3 is designed on the side, i.e. the bottom, of the collimator 2 opposing the semiconductor 1. The embodiments of the X-ray radiation detector shown in FIGS. 2, 4 and 5 each differ in the embodiment of the reflection layer 3. In FIG. 2 the reflection layer 3 is designed to be flat, with a uniform thickness, so that the surfaces of the reflection layer 3, of the collimator 2 and of the semiconductor 1 or of the electrode 4 are aligned parallel to one another. The reflectance of the reflection layer 3 is likewise uniform, so that the reflection of the IR radiation off the reflection layer 3 is uniform in the z direction.

In principle, the reflection layer 3 reflects the radiation which is incident into the gap 5 onto the semiconductor material 1 or onto the electrode 4 arranged on the semiconductor material 1. The radiation is partially reflected back by the electrode 4 multiple times to the reflection layer 3 and otherwise is transmitted into the semiconductor material 1. The proportion of the radiation transmitted into the semiconductor material 1 is dependent on the transmittance of the electrode 4. In the semiconductor material 1 additional charge carriers are generated by the radiation, with which the polarization of the semiconductor material 1 or the drift of the X-ray radiation detector occurring in the semiconductor 1 are equalized because of the X-ray radiation which is incident in operation.

Figure 3:
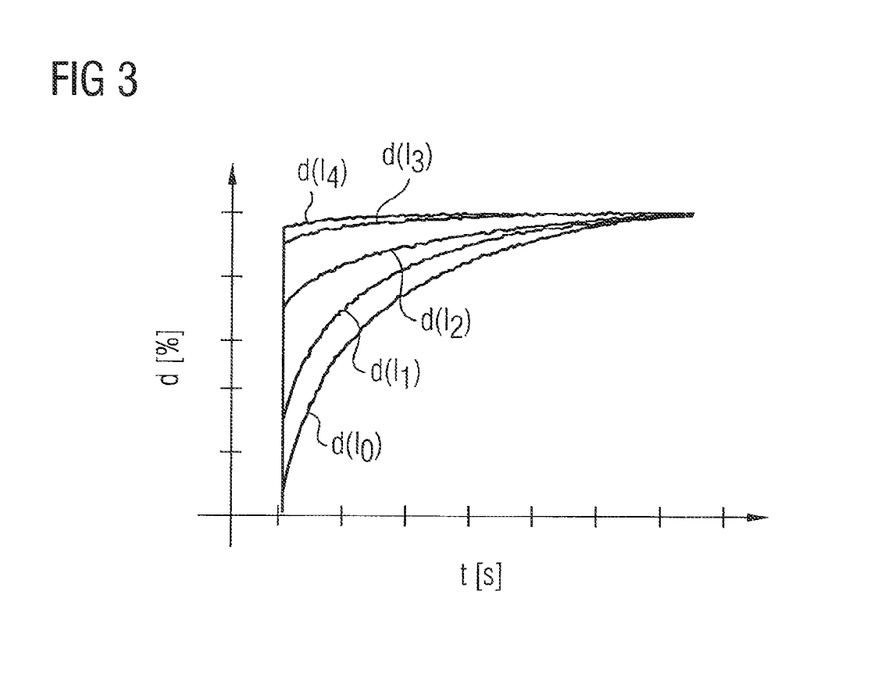
FIG. 3 shows a diagram of the change over time of the drift of an X-ray radiation detector as a function of the intensity of the additional radiation.

FIG. 3 shows the change over time in the drift of an X-ray radiation detector as a function of the intensity of the IR radiation. Plotted on the ordinate is the value of the drift d in percent and on the abscissa the time t in seconds. The lowest profile shows the drift behavior of a conventional X-ray radiation detector without irradiation with the additional radiation. The drift of the X-ray radiation detector increases until a virtually constant value is reached. The other profiles show the respective drift behavior during simultaneous irradiation by the light-emitting diode as the intensity increases. Due to the IR irradiation there is a clear reduction in drift, to the point at which drift is almost completely prevented in the X-ray radiation detector. Here the end value of the drift is reached significantly faster than without IR irradiation.

FIG. 4 shows the X-ray radiation detector with another embodiment of the reflection layer 3. The reflection layer 3 is here designed to be curved, wherein the concave curvature is geared to the light-emitting diode 6. In other words the reflection layer 3 is designed to be thicker at large z values than at small z values. The thickness of the curved reflection layer 3 therefore increases in the propagation direction of the IR radiation. The radiation pattern of the light-emitting diode 6 and the distance between the light-emitting diode 6 and the reflection layer 3 is taken into account in the design of the curvature. The height of the curvature virtually corresponds to the width of the gap 5. Thanks to the curvature a more uniform reflection of the IR radiation onto the semiconductor 1 is achieved, so that the charge carrier generation in the semiconductor 1 is uniform.

FIG. 5 shows another embodiment of the X-ray radiation detector. Here firstly the reflection layer 3 has a variable reflectance in the z direction or as the distance from the light-emitting diode 6 increases and secondly the electrode 4 has a variable transmittance in the z direction or as the distance from the light-emitting diode 6 increases. This is depicted schematically in FIG. 6. To vary the reflectance or the transmittance, several differently spaced openings are embodied in the reflection layer 3 or in the electrode 4.

Figure 6:
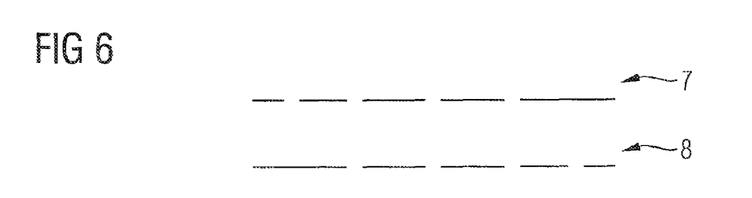
FIG. 6 shows respectively a schematic depiction of a reflection layer that varies in the z direction and of an electrode of the X-ray radiation detector according to FIG. 5.

In this embodiment the reflection layer 3 has four openings, whose spacing increases in the z direction (see curve 7). No reflection of the IR radiation takes place at the openings; the reflectance is therefore virtually zero. However, the electrode 4 has four openings, whose spacing becomes smaller in the z direction (see curve 8). The IR radiation is transmitted through the openings completely into the semiconductor material 1. Firstly therefore IR radiation is increasingly reflected in the z direction and secondly more IR radiation is transmitted into the semiconductor 1. Thanks to these changes, charge carriers are increasingly generated in the z direction, i.e. remote from the radiation source. Thus an irradiation of the reflection layer 3 which may be non-uniform in the z direction is equalized.

Although the invention has been further illustrated in detail using the preferred exemplary embodiment, the invention is not restricted by the disclosed examples and other variations can be derived therefrom by the person skilled in the art, without departing from the scope of protection of the invention.

The invention claimed is:

1. A direct-converting X-ray radiation detector for detecting X-ray radiation, the detector comprising:
   a semiconductor material to detect the X-ray radiation;
   at least one radiation source to irradiate the semiconductor material with additional radiation; and
   at least one collimator arranged in front of the semiconductor material in a beam path of the X-ray radiation, the at least one collimator including at least one reflection layer on a side facing the semiconductor material, the at least one reflection layer having material properties that vary as a distance from the at least one radiation source varies, and the at least one reflection layer configured to reflect the additional radiation uniformly onto the semiconductor material.

2. The X-ray radiation detector of claim 1, wherein a gap for the additional radiation is between the semiconductor material and the at least one collimator.

3. The X-ray radiation detector of claim 1, wherein the at least one reflection layer has a reflectance of at least 50%.

4. The X-ray radiation detector of claim 1, wherein the at least one reflection layer is flat.

5. A direct-converting X-ray radiation detector for detecting X-ray radiation, the detector comprising:
   a semiconductor material to detect the X-ray radiation;
   at least one radiation source to irradiate the semiconductor material with additional radiation; and
   at least one collimator arranged in front of the semiconductor material in a beam path of the X-ray radiation, the at least one collimator including at least one reflection layer on a side facing the semiconductor material, the at least one reflection layer including at least one curvature, and the at least one reflection layer configured to reflect the additional radiation uniformly onto the semiconductor material.

6. The X-ray radiation detector of claim 5, wherein material properties of the at least one reflection layer vary as a distance from the at least one radiation source varies.

7. The X-ray radiation detector of claim 1, wherein the at least one reflection layer has different material properties viewed in the propagation direction of the additional radiation.

8. The X-ray radiation detector of claim 1, further comprising:
   an electrode attached to the semiconductor material opposite the at least one reflection layer, the electrode including at least one opening.

9. The X-ray radiation detector of claim 1, wherein the at least one reflection layer is formed from at least one of reflector paint, metal, plastic, compounds, and semiconductors.

10. A CT system comprising the direct-converting X-ray radiation detector of claim 1.

11. A method for detecting incident X-ray radiation by way of a direct-converting X-ray radiation detector, the method comprising:
    indirectly and uniformly irradiating a semiconductor material with additional radiation via at least one reflection layer to generate additional charge carriers, the at least one reflection layer having material properties that vary as a distance from a source of the additional radiation varies; and
    detecting the incident X-ray radiation using the semiconductor material.

12. The method of claim 11, wherein a reflectance of the at least one reflection layer varies at least one of in the propagation direction of the additional radiation and in the z direction of the X-ray radiation detector.

13. The method of claim 11, wherein
    an electrode, which is attached to the semiconductor material opposite the at least one reflection layer, is used; and
    the electrode has a transmittance that varies at least one of in the propagation direction of the additional radiation and in the z direction of the X-ray radiation detector.

14. The method of claim 11, wherein the indirectly and uniformly irradiating a semiconductor material comprises:
    irradiating the semiconductor material at least one of before and during the incidence of the X-ray radiation.

15. A CT system comprising the direct-converting X-ray radiation detector of claim 2.

16. The X-ray radiation detector of claim 1, wherein the at least one reflection layer has a reflectance of at least 90%.

17. The X-ray radiation detector of claim 1, wherein the at least one reflection layer has a reflectance of at least 99%.

18. The X-ray radiation detector of claim 1, wherein the at least one reflection layer is formed from at least one of reflector paint, light metal, laminated plastic, metal alloys and semiconductors.

19. The method of claim 12, wherein
    an electrode, which is attached to the semiconductor material opposite the at least one reflection layer, is used; and
    the electrode has a transmittance that varies at least one of in the propagation direction of the additional radiation and in the z direction of the X-ray radiation detector.

20. The method of claim 12, wherein the indirectly and uniformly irradiating a semiconductor material comprises:
    irradiating the semiconductor material at least one of before and during the incidence of the X-ray radiation.

21. The X-ray radiation detector of claim 5, wherein a gap for the additional radiation is between the semiconductor material and the at least one collimator.

22. The X-ray radiation detector of claim 5, wherein the at least one reflection layer has a reflectance of at least 50%.

23. The X-ray radiation detector of claim 5, wherein the at least one reflection layer has different material properties viewed in the propagation direction of the additional radiation.

24. The X-ray radiation detector of claim 5, wherein the at least one reflection layer has a reflectance of at least 90%.

25. A method for detecting incident X-ray radiation by way of a direct-converting X-ray radiation detector, the method comprising:
   indirectly and uniformly irradiating a semiconductor material with additional radiation via at least one reflection layer to generate additional charge carriers, the at least one reflection layer having at least one curvature; and
   detecting the incident X-ray radiation using the semiconductor material.

* * * * *